(12) United States Patent
Minkara

(10) Patent No.: US 6,790,264 B2
(45) Date of Patent: Sep. 14, 2004

(54) CONTROL OF AMMONIA EMISSION FROM AMMONIA LADEN FLY ASH IN CONCRETE

(75) Inventor: Rafic Y. Minkara, Kennesaw, GA (US)

(73) Assignee: ISG Resources, Inc., Salt Lake City, UT (US)

(*) Notice: Subject to any disclaimer, the term of this patent is extended or adjusted under 35 U.S.C. 154(b) by 50 days.

(21) Appl. No.: 10/130,333

(22) PCT Filed: Mar. 7, 2001

(86) PCT No.: PCT/US01/07207
§ 371 (c)(1),
(2), (4) Date: Sep. 23, 2002

(87) PCT Pub. No.: WO01/66486
PCT Pub. Date: Sep. 13, 2001

(65) Prior Publication Data
US 2003/0205173 A1 Nov. 6, 2003

Related U.S. Application Data
(60) Provisional application No. 60/187,628, filed on Mar. 8, 2000.

(51) Int. Cl.$^7$ .............................................. C04B 18/06
(52) U.S. Cl. .................................. 106/705; 106/DIG. 1; 423/237; 423/238; 423/352; 73/23.2; 73/28.01; 436/9; 436/113
(58) Field of Search ........................ 106/DIG. 1, 705; 423/237, 238, 352; 73/23.2, 28.01; 436/9, 113

(56) References Cited

U.S. PATENT DOCUMENTS

| | | |
|---|---|---|
| 3,711,597 A | 1/1973 | Searfi et al. |
| 3,961,020 A | 6/1976 | Seki |
| 4,104,131 A | 8/1978 | Didycz et al. |
| 4,108,735 A | 8/1978 | Burcaw, Jr et al. |
| 4,650,587 A | 3/1987 | Polak et al. |

(List continued on next page.)

FOREIGN PATENT DOCUMENTS

| | | |
|---|---|---|
| DE | 3526756 A1 | 1/1987 |
| DE | 3711503 A1 | 10/1988 |
| DE | 3732026 A1 | 4/1989 |
| DE | 3802884 A1 | 8/1989 |
| JP | 56166978 | 12/1981 |
| JP | 57019078 | 2/1982 |
| JP | 59010327 | 1/1984 |
| JP | 59029024 | 2/1984 |
| JP | 59059237 | 4/1984 |

OTHER PUBLICATIONS

K. Ohlinger; T. Young; E. Schroeder; *Wastewater Chemnistry— Struvite Precipitation Kinetics*; Scope Newsletter; Mar. 2000; http://www.ceep-phosphates.org/scope/articles/scope36/scope36-06.htm; Scope No. 36; Internet Web site.

*Primary Examiner*—Paul Marcantoni
(74) *Attorney, Agent, or Firm*—Wegman, Hessler & Vanderburg

(57) ABSTRACT

The present invention relates to a pozzolanic admixture containing ammonia-laden fly ash, method for making the pozzolanic admixture and method for controlling ammonia gas ($NH_3$) emission from cementitious slurries using the pozzolanic admixture. The associated hypochlorite and ammonia reaction produces monochloramine and chloride salts at relatively low concentration levels harmless to concrete and concrete applications. The resulting monochloramine and chloride salt products are stable and do not dissipate into the air, thereby, eliminating odorous emission that is produced from cementitious slurry containing untreated ammonia laden fly ash. This invention relates to the method of adding hypochlorites ($OCl^-$) in the form of calcium hypochlorite—$Ca(OCl)_2$, lithium hypochlorite—LiOCl, sodium hypochlorite NaOCl or trichloro-s-triazinetrione—$C_3N_3O_3Cl_3$ to the ammonia-ladden fly ash at dosage levels, based on ammonia concentration in ash and stoichiometry, for a complete or partial oxidation of ammonia to eliminate, or respectively reduce, ammonia gas evolution from the high pH cementitious slurries.

18 Claims, 1 Drawing Sheet

U.S. PATENT DOCUMENTS

| | | | |
|---|---|---|---|
| 4,780,289 A | 10/1988 | Epperly et al. | |
| 5,019,360 A | 5/1991 | Lehto | |
| 5,132,027 A | 7/1992 | Ukawa et al. | |
| 5,141,732 A | 8/1992 | Haardt et al. | |
| 5,211,853 A | 5/1993 | Jackson et al. | |
| 5,232,604 A | 8/1993 | Swallow et al. | |
| 5,294,348 A | 3/1994 | Horny et al. | |
| 5,330,544 A | 7/1994 | Thomson et al. | |
| 5,346,549 A | 9/1994 | Johnson | |
| 5,362,319 A | 11/1994 | Johnson | |
| 5,512,257 A | 4/1996 | Frey | |
| 5,525,317 A | 6/1996 | Bhat et al. | |
| 5,568,895 A * | 10/1996 | Webb et al. | 241/16 |
| 5,618,511 A | 4/1997 | Randolph et al. | |
| 5,695,616 A | 12/1997 | Helfritch et al. | |
| 5,766,337 A | 6/1998 | Moon | |
| 5,830,422 A | 11/1998 | Kresnyak et al. | |
| 5,837,052 A | 11/1998 | Oates et al. | |
| 5,840,085 A | 11/1998 | Tokunaga et al. | |
| 5,840,179 A | 11/1998 | Minkara et al. | |
| 5,906,803 A | 5/1999 | Leppalahti | |
| 6,077,494 A | 6/2000 | Gasiorowski et al. | |
| 6,290,066 B1 | 9/2001 | Hwang | |

* cited by examiner

CONTROL OF AMMONIA EMISSION FROM AMMONIA LADEN FLY ASH IN CONCRETE

CROSS-REFERENCE TO RELATED APPLICATIONS

Priority filing benefit of (1) International PCT application PCT/US01/07207 filed Mar. 7, 2001, and published under PCT 21(2) in the English language and (2) U.S. Provisional Application Serial No. 60/187,628 filed Mar. 8, 2000.

BACKGROUND OF THE INVENTION

Fly ash produced at coal fired power plants is commonly used in ready-mixed concrete as a pozzolanic admixture and for partial replacement for cement. Fly ash consists of alumino-silicate glass that reacts under the high alkaline condition in cementitious slurry to form additional cementitious compounds when the fly ash is added to the cementitious slurry. Fly ash is an essential component in high performance concrete. Fly ash contributes many beneficial characteristics to cementitious compounds including increased density, long term strength, decreased permeability, improved durability against chemical attack, and improved workability of freshly placed material.

Coal burning power stations commonly inject ammonia or ammonia based reagents into associated flue gas containing fly ash in an effort to: (1) enhance electrostatic precipitator (ESP) performance to reduce opacity and (2) remove nitrous oxide ($NO_x$) using selective catalytic reduction (SCR) and selective non-catalytic reduction (SNCR) technologies to meet $NO_x$ emission regulations. Ammonia injection into the flue gas for ESP, SCR and SNCR performance enhancement commonly results in the deposition of ammonia on the fly ash. Also, gas phase reaction of SOx and $NH_3$ in the flue gas results in the deposition of ammonium salts on the fly ash in the form of ammonium sulfate—$(NH_4)_2SO_4$ and ammonium bisulfate—$NH_4HSO_4$. In both SCR and SNCR processes, $NO_x$ is reduced using ammonia to produce nitrogen gas ($N_2$) and water ($H_2O$) vapor according to the following reaction:

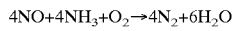

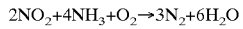

The degree of ammonia contamination in the fly ash, and associated concentration levels, vary among power plants depending on the rate of ammonia injection, the performance of SCR or SNCR process, the amount of $SO_3$ in the flue gas and the associated operating conditions of the boiler and air pollution control devices. It has been observed that fly ash produced from high sulfur eastern bituminous coal (Class F fly ash) adsorbs more ammonia than fly ash produced from low sulfur western sub-bituminous coal (Class C fly ash). As previously mentioned, the presence of sulfur in the flue gases increases the associated deposition of ammonia in the form of $(NH_4)_2SO_4$ and $NH_4HSO_4$. The high alkaline condition of Class C ash inhibits ammonia cation ($NH_4^+$) formation. Typical ammonia concentrations on fly ash, as a result of ammonia injection, ranges between 50–120 mg/kg for SCR generated fly ash, 250–600 mg/kg for SNCR generated fly ash, and 700–1200 mg/kg for ESP generated fly ash.

When ammonia-laden fly ash is used in cementitious slurry applications, the ammonium salts dissolve in water to form ammonia cations ($NH_4^+$). Under the high pH (pH>12) condition created by cementitious alkali, ammonium cations ($NH_4^+$) are converted to dissolved ammonia gas ($NH_3$). Ammonia gas evolves from the fresh cementitious slurry into the air, exposing workers. The rate of ammonia gas evolution depends on ammonia concentration, mixing intensity, exposed surface, and ambient temperature. Ammonia has no measurable effect on concrete quality (strength, permeability, etc.). Ammonia gas odors could range from mildly unpleasant to a potential health hazard. Ammonia odors are detected by the human nose at 5 to 10 ppm levels. The OSHA threshold and permissible limits are set at 25 and 35 ppm for the time weighted average—eight-hour (TWA 8-hr) and the short term exposure limit—fifteen-minute (STEL 15-min), respectively. Ammonia gas concentration of 150–200 ppm can create a general discomfort. At concentrations between 400 and 700 ppm ammonia gas can cause pronounced irritation. At 500 ppm, and above, ammonia gas is immediately dangerous to health; at 2,000 ppm, death can occur within minutes.

Other than OSHA exposure limits, there are no regulatory, industry or ASTM standards or guidelines for acceptable levels of ammonia in fly ash. However, based on industry experience, fly ash with ammonia concentration at less than 100 mg/kg does not appear to produce a noticeable odor in ready-mix concrete. Depending on site and weather conditions, fly ash with ammonia concentration ranging between 100–200 mg/kg could result in unpleasant or unsafe concrete placement and finishing work environment. Fly ash with ammonia concentration exceeding 200 mg/kg produces unacceptable odor when used in ready-mixed concrete applications.

In addition to the risk of human exposure to ammonia gas evolving from cementitious slurry produced using ammonia-laden ash, the disposal of the ammonia-laden fly ash in landfills and ponds at coal burning power stations also creates potential risks to humans and the environment. Ammonium salt compounds in fly ash are extremely soluble. Upon contact with water, the ammonium salts leach into the water and are carried to ground water and nearby rivers and streams causing potential environmental damage such as ground water contamination, fish kill and eutrophication. Ammonia gas could also evolve upon wetting of alkaline fly ashes, such as those generated from the combustion of western sub-bituminous coal. Water conditioning and wet disposal of alkaline, ammonia-laden, fly ash exposes power plant workers to ammonia gas.

SUMMARY OF THE INVENTION

The present invention relates to the addition of a chemical oxidizing agent to dry fly ash containing concentrations of ammonia. The chemical can be added and blended with the dry fly ash at any point between the fly ash collection system at the power plant and final delivery to the ready-mixed customer, or at the point of use at the ready-mixed customer site. The pre-blended chemical oxidizing agent does not react with ammonia in the dry fly ash; the chemical oxidizing agent is released during the wet slurry mixing process. Once the ammonia-laden fly ash is introduced in the cementitious slurry, ammonium salts from the ammonia-laden fly ash dissolve. The high alkaline (high pH) condition of the cementitious slurry converts the ammonium cations ($NH_4^+$) to dissolved ammonia gas ($NH_3$). Without the chemical oxidizing agent, ammonia gas ($NH_3$) evolves from the cementitious slurry during mixing, transportation, pouring and placement.

More specifically, this invention relates to pre-treated ammonia-laden fly ash and to methods of treating the ammonia-laden fly ash. Addition of the chemical oxidizing agent with the dry ammonia-laden fly ash prior to incorporating the fly ash into cementitious slurries results in chemical conversion, via oxidation, of ammonia into harmless products. Thereby, the exposure risk of the ammonia gases ($NH_3$) is limited.

The preferred chemical treatment reagents are strong oxidizers such as hypochlorites ($OCl^-$) commonly found in the form of $Ca(OCl)_2$, NaOCl, LiOCl, trichloro-s-triazinetrione (trichlor), etc. and are added to the ammonia-laden fly ash. Preferably, the oxidizers are added in dry form to the fly ash, but it is also possible to spray a dilute solution (containing up to about 30% oxidizer) onto the fly ash. At present, calcium hypochlorite is preferred. The reagent is activated upon water addition and reacts with dissolved ammonia in the ash or concrete slurry to form primarily monochloramine ($NH_2Cl$). An overdose of the hypochlorite reagent would further oxidize monochloramine to form nitrogen gas ($NH_2$) and chlorides.

As used herein, the phrase hypochlorite containing oxidizer is used to denote compounds that include the hypochlorite moiety or form such moiety upon addition of water. For example, the trichor compound forms hypochlorous acid and cyanuric acid upon water addition. At elevated pHs, the hypochlorous acid ionizes to the hypochlorite ion.

The basic aqueous phase ammonia oxidation reaction using hypochlorite is as follows:

$$NH_4^+ + OCl^- \rightarrow NH_2Cl + H_2O$$

The rate of ammonia oxidation by hypochlorite depends upon pH, temperature, time, initial dosage and the presence of competing reducing agents. The pH condition of this reaction in Portland cement based concrete and mortar is governed by the presence of alkali from the associated cement hydration. The expected cementitious slurry pH is between 12 and 14. The temperature of freshly mixed concrete tends to be slightly warmer than the ambient temperature as a result of the heat of hydration. The optimum concrete temperature is in the range of 10 to 15° C. (50 to 60° F.), or lower for massive concrete pours, to avoid thermal cracking. Concrete temperature should not exceed 33° C. (90° F.). Time of reaction is also governed by conventional and standard concrete practices namely mixing, handling and placing guidelines. Ready-mixed concrete batches are mixed for at least 5 to 10 minutes. ASTM C94 requires the concrete to be placed within 90 minutes of mixing. The ammonia, in ammonia-laden fly ash and concrete mixtures, represents the most readily available reducing agent to react with hypochlorite. The chloramine forming reaction of ammonia and hypochlorite in water are 99% complete within a few minutes. Theoretically, a 1:1 molar ratio of hypochlorite to ammonia (Cl:N) is needed to produce monochloramine. Further increases in the molar ratio of Cl:N result in further oxidation and formation of nitrogen gas and chloride salts.

Fly ash and Portland cement are produced under strong oxidizing conditions in boilers and kilns. Therefore, the fly ash and Portland cement tend to be void of any reducing agents during production; ammonia is introduced into the fly ash in post-combustion air pollution control devices. Concrete aggregates (i.e., sand and gravel) should be free of deleterious organic substances that could otherwise exert a demand on hypochlorite. The presence of some organic admixtures in concrete (e.g., air entraining and water reducing agents) do not present any measurable demand on hypochlorite since ammonia is a strong reducing agent and the desired product, monochloramine, is also a reducing agent.

Other advantages and benefits will be apparent to one skilled in the art when reviewing the specification in combination with the drawings as described herein.

BRIEF DESCRIPTION OF THE DRAWING

The invention is more readily understood and appreciated by reference to the following FIGURE.

DETAIL DESCRIPTION OF THE INVENTION

Figure 1:
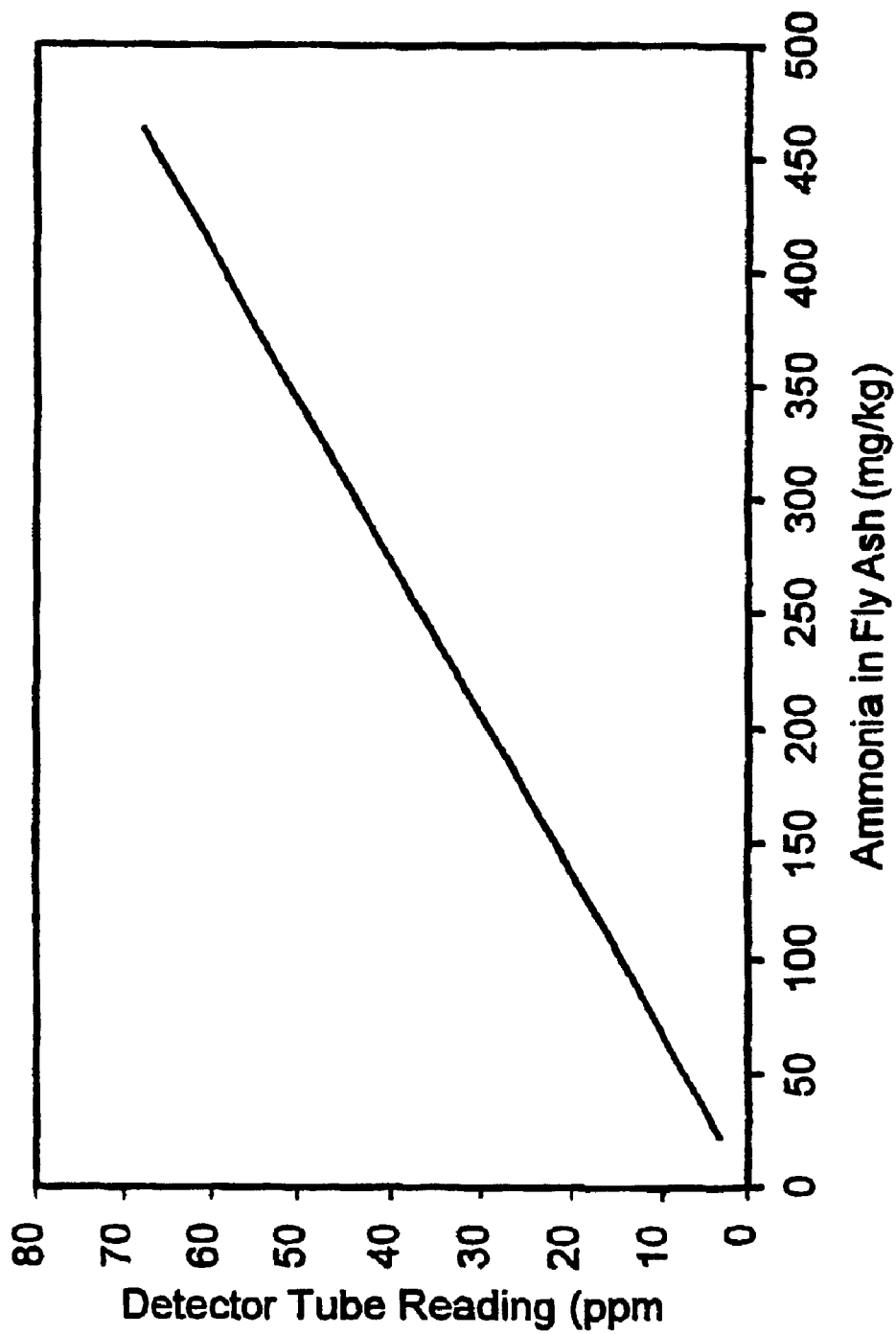
FIG. 1 is a graph, resulting from the rapid screening test procedure in accordance with the present invention, showing detector tube reading versus ammonia in fly ash.

A molar dosage of Cl:N between 0.25:1 and 3:1, preferably between 1:1 and 2:1, and most preferably 1.5:1, is sufficient to reduce ammonia and prevent ammonia gas evolution from cementitious mixtures containing ammonium compounds. For example, using 1:1 molar ratio, the theoretical amount, in kilograms (kg.), of $Ca(OCl)_2$ per ton of ash needed to oxidize 100 mg/kg, as N ammonia to monochloramine, is 0.51. In the case of lithium hypochlorite (LiOCl), and using 1:1 molar ratio, the theoretical amount, in kg, of LiOCl per ton of ash needed to oxidize 100 mg/kg, as N ammonia to monochloramine, is 0.42.

The composition in accordance with the present invention and the methods of making and using the composition are now illustrated with the aid of the following examples, which are included for illustration purposes only and are not meant to limit the invention.

EXAMPLE 1

The results of the effectiveness of oxidation using $Ca(OCl)_2$ at various Cl:N molar ratios are presented in TABLE 1; the results are for fly ash (20%) and cement (80%) mixed with water in a 1 liter flask. The ammonia concentration in the fly ash used in this experiment is 600 mg/kg. The ammonia gas ($NH_3$) concentration in the closed head-space of the flask was measured according to the rapid test procedure described below. Samples of the headspace gas were extracted through a Drager® detector tube, or equivalent device, after 2 minutes of mixing.

TABLE 1

| Cl:N Molar Ratio | $NH_3$ Gas Concentration |
|---|---|
| 0:1 | >70 ppm |
| 0.25:1 | 65 ppm |
| 0.50:1 | 55 ppm |
| 0.75:1 | 50 ppm |
| 1:1 | 30 ppm |
| 1.5:1 | 7.5 ppm |
| 2:1 | 2.5 ppm |

EXAMPLE 2

The results of the effectiveness of oxidation using $Ca(OCl)_2$ at various Cl:N molar ratios are presented in TABLE 2; the results are for mortar mixes consisting of 30% cementitious materials (cement and fly ash at 20% replacement), 70% sand and 0.6 w/c (water to cementitious materials) ratio. The ammonia concentration in the fly ash used in the mortar mixes tested at 300 mg/kg. The ammonia gas ($NH_3$) evolution was measured immediately after mixing (t=0), at 5 minutes after mixing and 10 minutes after mixing using Drager® detector tubes, or equivalent. NT indicates no test performed.

TABLE 2

| Cl:N Molar Ratio | NH$_3$ at t = 0 min | NH$_3$ at t = 5 min | NH$_3$ at t = 10 min |
| --- | --- | --- | --- |
| 0:1 | 50 ppm | 50 ppm | 50 ppm |
| 0.5:1 | NT | 40 ppm | NT |
| 1:1 | 40 ppm | 30 ppm | 20 ppm |
| 1.5:1 | 20 ppm | NT | 5 ppm |
| 2:1 | 20 ppm | 2.5 ppm | 2.5 ppm |
| 3:1 | NT | 0 ppm | 0 ppm |

EXAMPLE 3

The results of the effectiveness of oxidation using Ca(OCl)$_2$ in concrete mixes containing fine and coarse aggregates at Cl:N molar ratios of 0:1 (no treatment), 1.5:1 and 2:1 are presented in TABLE 3; the results are for concrete mixes consisting of 13% cementitious materials (cement and fly ash at 20% replacement), 38% sand, 49% gravel and 0.6 w/c (water to cementitious materials) ratio. The ammonia concentration in the fly ash used in the mixes tested at 600 mg/kg. The ammonia gas (NH$_3$) evolution was measured immediately after mixing (t=0) and at 15 minutes after mixing using Drager® detector tubes, or equivalent.

TABLE 3

| Cl:N Molar Ratio | NH$_3$ at t = 0 min | NH$_3$ at t = 15 min |
| --- | --- | --- |
| 0:1 | >70 ppm | >70 ppm |
| 1.5:1 | 10 ppm | 5 ppm |
| 2:1 | 2.5 ppm | 0 ppm |

A rapid screening test procedure was developed as an integral part of the present invention to determine the concentration of ammonia in the ammonia-laden fly ash. The rapid screening test procedure requires obtaining a representative sample of fly ash. A predetermined amount of fly ash is mixed with a known volume of water in a closed beaker to dissolve the ammonium salts. The pH of the fly ash and water slurry is raised using sodium hydroxide to over 12.0 to convert ammonium cations (NH$_4^+$) to ammonia gas (NH$_3$). The ammonia gas concentration in the closed headspace of the flask is measured using disposable ammonia gas detector tubes. A sample of the headspace gas is extracted through the detector tube using a handheld air sample extraction pump. The ammonia gas concentration in the beaker headspace is determined by the color change, usually yellow to blue, on the graduated detector tube. The ammonia gas concentration measured by the detector tube is directly related to the concentration of ammonia in the ash placed in the beaker.

The ammonia gas concentration measured using the rapid screening test procedure, in accordance with the present invention, has no direct relation to the ammonia gas concentration detected in ready-mixed concrete trucks or to the ammonia gas emitted from freshly poured concrete; this procedure only gives an indication to the amount of ammonia present in fly ash. Actual concentrations of ammonia out-gassing from large volumes of freshly mixed and poured concrete structures would depend on the ammonia concentration in ash, the ash content of the concrete, the size of concrete structure, the location of the pour (e.g. below grade vs. above grade), and weather conditions such as ambient temperature and, especially, wind speed. The rapid screening test procedure is most useful to determine the potential of ammonia out-gassing and to evaluate mitigation options such as treatment with an oxidizing compound.

The materials needed to perform the rapid screening test procedure include: stir plate, 1000 ml Erlenmeyer flask, stopper, stir bar, de-ionized or distilled water, detector tubes for ammonia with 0–100 ppm measuring range such as Drager® tubes, or equal, hand pump for the detector tubes such as Drager® Accuro bellows pump, or equal, 1 N sodium hydroxide, pipette and graduated cylinders.

The rapid screening test procedure is as follows: (1) collect a representative dry sample of fly ash using a core sampler or siphon tube according to ASTM C702; (2) place 100 ml of water in a clean 1000 ml Erlenmeyer flask; (3) weigh out 25 g of the fly ash material and add to the water while stirring on a stir plate in the Erlenmeyer flask; (4) close the flask and allow the slurry to stir for 1 minute; (5) add 10 ml of 1 N sodium hydroxide using a pipette and immediately stopper the flask, allow the slurry to stir for 1 minute; the pH of the solution should exceed 12; if needed, add more sodium hydroxide to bring the pH to 12; (6) prepare the ammonia detector tube for testing according to manufacturer directions; (7) insert the tube tightly in the hand pump making sure that the arrow on the tube points toward the pump; (8) insert the other end of the tube into the stopper hole mid-way into the flask making sure that it is not immersed in the liquid; (9) extract a gas sample through the detector tube by operating the hand pump according to manufacturer directions; and (10) read the entire length of the discoloration immediately. The color change should be from yellow to blue. The reading on the tube indicates the ammonia gas concentration in the beaker headspace in ppm. A chart, as depicted in FIG. 1, is used to estimate the ammonia concentration in the fly ash (mg/kg) based on the ammonia detector tube reading (ppm). The chart of FIG. 1 was developed using ash samples with known ammonia concentrations. The rapid screening test procedure and the FIG. 1 chart are used to screen the ash and determine the level of chemical oxidizer treatment needed using this invention.

The effects of oxidation treatment on concrete quality are positive. Monochloramine is highly soluble, stable and does not effectively dissipate in the air. Monochloramine does not disassociate into ions. It is a safe and commonly produced compound for drinking water disinfection.

Overdosing of hypochlorite would result in further oxidation of monochloramine (NH$_2$Cl) to dichloramine (NHCl$_2$) and then to trichloramine or nitrogen trichloride (NCl$_3$). Theoretically, it should require 3 moles of OCl for the complete conversion of NH$_3$ to NCl$_3$. Further overdosing of hypochlorite (molar ratio larger than 3:1) to complete the oxidation would produce nitrogen N$_2$ and nitrous oxide NO$_2$ gaseous products and soluble chlorides. In the case of the reagent calcium hypochlorite Ca(OCl)$_2$, overdosing would ultimately produce calcium chloride CaCl$_2$. Calcium chloride is commonly used, at much higher concentrations (2% by weight of cement), as a concrete admixture to accelerate early strength gain. The amount of soluble chlorides added to concrete in overdose circumstances is correspondingly low. For example, using an unlikely overdose equivalent to a 5:1 molar ratio to treat fly ash containing 300 mg/kg ammonia, the amount of Ca(OCl)$_2$ added would be 6.12 kg per ton of fly ash. Assuming complete oxidation to nitrogen gas and calcium chloride, the amount of calcium chloride introduced is calculated at 4.75 kg of CaCl$_2$ per ton of fly ash which is less than 0.1% by weight of cementitious materials based on 20% cement replacement. Based on this example, the amount of chlorides introduced to a typical concrete mix is about 0.01% or 100 ppm.

The effects of oxidation treatment using Ca(OCl)$_2$ on concrete compressive strength was evaluated using mortar mixes with fly ash treated with 0, 2.4, 3.6, and 4.8 grams of $Ca(OCl)_2$ per ton of ash. The compressive strength results are shown, in TABLE 4, in MPa for 3, 7, 14 and 28 days.

TABLE 4

| Cl:N Molar Ratio | g $Ca(OCl)_2$/kg ash | 3-day | 7-day | 14-day | 28-day |
| --- | --- | --- | --- | --- | --- |
| 0:1 | 0 | 20.2 | 23.8 | 27.0 | 25.1 |
| 1:1 | 2.4 | 21.0 | 23.4 | 26.7 | 24.3 |
| 1.5:1 | 3.6 | 20.6 | 24.3 | 24.5 | 24.5 |
| 2:1 | 4.8 | 22.9 | 24.3 | 29.1 | 25.6 |

Cementitious compositions in accordance with the invention comprise a cementitious component such as Portland cement, fly ash, and an oxidizer for controlling ammonia gas evolution from the mix. The cementitious component may be present in a broad range of about 1–99 wt %, with the fly ash present in an amount of about 1–99 wt %. The oxidizer is present in a molar amount relative to the ammonia content of the fly ash as is stated above.

While there is shown and described the present preferred examples of the inventive compositions and methods, it is to be understood that the invention is not limited thereto, but may be otherwise variously practiced within the scope of the following claims.

What is claimed is:

1. A method for reducing ammonia gas evolution from cementitious slurries when ammonia-laden fly ash is added to the slurry, comprising the steps:
   a) blending an oxidizer with said ammonia-laden fly ash to form a mixture; and
   b) mixing said oxidizer and ammonia-laden fly ash mixture with said cementitious slurry at a pH of about 12 to about 14 to thereby form stable reaction products that do not dissipate into the air and to reduce said ammonia gas evolution.

2. A method according to claim 1, wherein said oxidizer is a hypochlorite containing oxidizer.

3. A method according to claim 2, wherein said hypochlorite containing oxidizer comprises a member selected from the group consisting of calcium hypochlorite, sodium hypochlorite, lithium hypochlorite and trichloro-s-triazinetrione and mixture thereof.

4. A method according to claim 3, wherein said oxidizer is blended with said ammonia-laden fly ash in a molar amount of 0.25:1 to about 3:1 based upon Cl:N.

5. A method according to claim 4, wherein said oxidizer is blended in an amount of about 1:2 to about 2:1 of Cl:N.

6. A method according to claim 5, wherein said oxidizer is blended in an amount of about 1.5:1 Cl:N.

7. A method according to claim 3, wherein said hypochlorite containing oxidizer comprises calcium hypochlorite.

8. A method as recited in claim 1, wherein said mixing is conducted at a temperature of about 50° F. to about 90° F.

9. A method for reducing ammonia gas evolution from cementitious slurries when ammonia-laden fly ash is added to the slurry, comprising the steps:
   a) determining the concentration of ammonia in said ammonia-laden fly ash;
   b) blending a quantity of an oxidizer with said ammonia-laden fly ash, wherein said quantity of oxidizer is selected based on said concentration of ammonia;
   c) then, mixing said oxidizer and ammonia-laden fly ash mixture with said cementitious slurry at a pH of about 12 to about 14 wherein said oxidizer oxidizes ammonia in said ammonia-laden fly ash upon mixing said oxidizer and ammonia-laden fly ash mixture with said slurry to thereby form stable products that do not dissipate into the air; and
   d) depositing said mixed slurry for curing.

10. A method according to claim 9, wherein said concentration of ammonia in said ammonia-laden fly ash is determined via a rapid screening test procedure.

11. A rapid screening test procedure for determining the content of ammonia in ammonia-laden fly ash, including the following steps:
   a) collecting a representative dry sample of said ammonia-laden fly ash according to ASTM C702;
   b) placing 100 ml of water in a clean 1000 ml flask;
   c) weighing out 25 g of said ammonia-laden fly ash and adding said fly ash to said water while stirring on a stir plate in said flask;
   d) closing said flask and allowing said water and said fly ash to stir for 1 minute
   e) opening said flask and adding 10 ml of 1 N sodium hydroxide and immediate stoppering the flask; allowing said water, fly ash and said sodium hydroxide to stir for 1 minute; testing the pH of said water and said fly ash; and, if needed, adding more sodium hydroxide to bring the pH to 12;
   f) preparing the ammonia detector rube for testing;
   g) inserting said detector tube into a hand pump;
   h) inserting said detector tube into a stopper hold, into said flask;
   i) extracting a gas sample through said detector tube via said hand pump; and
   j) reading the entire length of the discoloration immediately.

12. A method comprising mixing (a) ammonia laden fly ash, (b) cement, (c) oxidizer, and (d) water to form a slurry, said oxidizer oxidizing said ammonia upon mixing of said water to reduce ammonia gas evolution from said slurry.

13. A method for reducing ammonia gas evolution from a cementitious slurry when ammonia-laden fly ash is added to the slurry, comprising the steps:
   a) blending a hypochlorite containing oxidizer with said ammonia-laden fly ash to form a mixture; and
   b) mixing said oxidizer and ammonia-laden fly ash mixture with said cementitious slurry wherein said oxidizer oxidizes ammonia in said ammonia-laden fly ash upon wetting said mixture while forming said cementitious slurry to reduce said ammonia gas evolution.

14. A method according to claim 13, wherein said hypochlorite containing oxidizer comprises a member selected from the group consisting of calcium hypochlorite, sodium hypochlorite, lithium hypochlorite and trichloro-s-triazinetrione and mixture thereof.

15. A method according to claim 14, wherein said oxidizer is blended with said ammonia-laden fly ash in a molar amount of about 1:2 to about 2:1 of Cl:N.

16. A method according to claim 13 further comprising determining the concentration of ammonia in said ammonia-laden fly ash and wherein the step of blending the oxidizer comprises blending a quantity of the oxidizer with said ammonia-laden fly ash, wherein said quantity of oxidizer is selected based on the concentration of ammonia in the fly ash.

17. A method according to claim 13 wherein said oxidizer and ammonia-laden fly ash mixture is mixed with said cementitious slurry at a pH of about 12 to about 14.

18. A method for in-situ oxidation of ammonia in ammonia-laden fly ash to reduce ammonia gas evolution when the ammonia-laden fly ash is wetted, the method comprising blending a hypochlorite containing oxidizer with said ammonia-laden fly ash to form a mixture and mixing said oxidizer and ammonia-laden fly ash mixture with water to form a slurry, wherein said oxidizer oxidizes ammonia in said ammonia-laden fly ash upon wetting to reduce said ammonia gas evolution.

* * * * *

UNITED STATES PATENT AND TRADEMARK OFFICE
CERTIFICATE OF CORRECTION

PATENT NO. : 6,790,264 B2
DATED : September 14, 2004
INVENTOR(S) : Rafic Y. Minkara It is certified that error appears in the above-identified patent and that said Letters Patent is hereby corrected as shown below:

Title page,
Item [57], ABSTRACT,
Line 16, delete "ammonia-ladden" and substitute -- ammonia-laden --.

Column 8,
Line 29, delete "rube" and substitute -- tube --.

Signed and Sealed this

Seventh Day of December, 2004

JON W. DUDAS
*Director of the United States Patent and Trademark Office*